United States Patent [19]

Adams et al.

[11] Patent Number: 5,207,219
[45] Date of Patent: May 4, 1993

[54] ATRIAL DEFIBRILLATOR AND METHOD FOR PROVIDING INTERVAL TIMING PRIOR TO CARDIOVERSION

[75] Inventors: John M. Adams, Issaquah; Clifton A. Alferness; Kenneth R. Infinger, both of Redmond; Joseph M. Bocek, Seattle, all of Wash.

[73] Assignee: InControl, Inc., Redmond, Wash.

[21] Appl. No.: 965,195

[22] Filed: Oct. 23, 1992

[51] Int. Cl.⁵ .............................................. A61N 1/39
[52] U.S. Cl. .............................................. 128/419 D
[58] Field of Search ................................. 128/419 D

[56] References Cited

U.S. PATENT DOCUMENTS

| | | | |
|---|---|---|---|
| 3,738,370 | 6/1973 | Charms | 128/419 D |
| 3,952,750 | 4/1976 | Mirowski et al. | 128/419 D |
| 3,985,142 | 10/1976 | Wickham | 128/419 PG |
| 5,107,850 | 4/1992 | Olive | 128/419 D |
| 5,165,403 | 11/1992 | Mehra | 128/419 D |

Primary Examiner—Kyle L. Howell
Assistant Examiner—Kennedy J. Schaetzle
Attorney, Agent, or Firm—Foley & Lardner

[57] ABSTRACT

An implantable atrial defibrillator provides cardioverting electrical energy to the atria of a human heart in need of cardioversion. The atrial defibrillator includes a first detector for detecting ventricular activations of the heart, a second detector for detecting atrial activity of the heart, and an atrial fibrillation detector responsive to the second detector for determining when the atria of the heart are in need of cardioversion. The atrial defibrillator also includes a cardioverting stage for applying the cardioverting electrical energy to the atria of the heart when the atria of the heart are in need of cardioversion and when the time between immediately successive ventricular activations is greater than a preselected minimum time interval.

13 Claims, 2 Drawing Sheets

ATRIAL DEFIBRILLATOR AND METHOD FOR PROVIDING INTERVAL TIMING PRIOR TO CARDIOVERSION

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may result from the mistimed delivery of cardioverting electrical energy to the atria of the heart. More specifically, the atrial defibrillator of the present invention guards against applying cardioverting electrical energy to the atria of the heart under conditions believed to contribute to induced ventricular fibrillation.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved atrial defibrillators and lead systems which exhibit both automatic operation and improved safety are fully described in copending U.S. application Ser. Nos. 07/685,130, filed Apr. 12, 1991, in the names of John M. Adams and Clifton A. Alferness for IMPROVED ATRIAL DEFIBRILLATOR AND METHOD and Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. As disclosed in the aforementioned referenced applications, synchronizing the delivery of the defibrillating or cardioverting electrical energy to the atria with a ventricular electrical activation (R wave) of the heart is important to prevent induced ventricular fibrillation. Ventricular fibrillation is a fatal arrhythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection assure reliable synchronization.

Another measure for reducing the risk of inducing ventricular fibrillation during the delivery of cardioverting electrical energy to the atria of the heart employed by the defibrillators of the aforementioned referenced applications is the reduction of the amount of the electrical energy which is passed through the ventricles during cardioversion of the atria. This is achieved by locating the cardioverting electrodes in or near the heart to provide a cardioverting energy path which confines most of the cardioverting electrical energy to the atria of the heart.

The atrial defibrillator and method of the present invention provides a further improvement to the end of safety and reduction in the risk of inducing ventricular fibrillation during atrial cardioversion or defibrillation. It has been observed that during episodes of atrial fibrillation, the cardiac rate increases to a high rate and/or becomes extremely variable. At high cardiac rates, the R wave of each cardiac cycle becomes closely spaced from the T wave of the immediately preceding cardiac cycle. This may lead to a condition known in the art as an "R on T" condition which is believed to contribute to induced ventricular fibrillation if the atria are cardioverted in synchronism with the R wave close to the T wave. During highly variable cardiac rates, a long cardiac cycle can be followed by a relatively short cardiac cycle. This condition in conjunction with a high cardiac rate is believed to cause a dispersion of refractoriness and also can result in an increased vulnerability to ventricular fibrillation. For a more complete understanding of the aforementioned highly variable cardiac rate and the consequences thereof, reference may be had to an article entitled El-Sherif et al., Reentrant Ventricular Arrhythmias in the Late Myocardial Infarction Period: Mechanism by Which a Short-Long-Short Cardiac Sequence Facilitates the Induction of Reentry, *Circulation*, 83(1): 268–278 (1991).

The atrial defibrillator and method of the present invention greatly reduces the risk of inducing ventricular fibrillation during atrial cardioversion or defibrillation by avoiding applying the cardioverting electrical energy to the atria at those instances when increased vulnerability to ventricular fibrillation may be present. As will be seen hereinafter, this is accomplished by interval timing prior to applying the cardioverting or defibrillating electrical energy. The time interval between immediately successive R waves is timed and the cardioverting or defibrillating electrical energy is only applied when a timed interval is greater than a preselected minimum interval. This provides protection for the increased vulnerability to ventricular fibrillation condition resulting from a high cardiac rate. To provide protection for the R on T condition resulting from a highly variable cardiac rate, a further condition may be applied to the timed interval requiring the timed interval to also be less than a preselected maximum interval before the cardioverting or defibrillating energy is applied to the atria.

SUMMARY OF THE INVENTION

The present invention therefore provides an atrial defibrillator for providing cardioverting electrical energy to the atria of a human heart. The atrial defibrillator includes detecting means for detecting ventricular activations of the heart and cardioverting means for applying the cardioverting electrical energy to the atria of the heart when the time between immediately successive ventricular activations detected by the detecting means is greater than a preselected minimum time interval.

The present invention further provides an implantable atrial defibrillator for providing cardioverting electrical energy to the atria of a human heart in need of cardioversion. The atrial defibrillator includes first detecting means for detecting ventricular activations of the heart and second detecting means for detecting atrial activity of the heart. The atrial defibrillator further includes atrial defibrillation detecting means responsive to the second detecting means for determining when the atria of the heart are in need of cardioversion and cardioverting means for applying the cardioverting electrical energy to the atria of the heart when the atria of the heart are in need of cardioversion and when the time between immediately successive ventricular activations is greater than a preselected minimum time interval.

In accordance with another aspect of the present invention, the atrial defibrillator cardioverting means applies the cardioverting electrical energy to the atria of the heart when the atria of the heart are in need of cardioversion and when the time between the immediately successive ventricular activations is greater than the preselected minimum time interval and less than a preselected maximum time interval.

The present invention still further provides a method of applying cardioverting electrical energy to the atria of a human heart in need of cardioversion. The method includes the steps of detecting ventricular activations of the heart, detecting atrial activity of the heart, and determining, responsive to the detected atrial activity of the heart, when the atria of the heart are in need of cardioversion. The method further includes the step of applying the cardioverting electrical energy to the atria of the heart when the atria of the heart are in need of cardioversion and when the time between immediately successive ventricular activations is greater than a preselected minimum time interval.

In accordance with still another aspect of the present invention, the applying step further includes applying the cardioverting electrical energy to the atria of the heart when the atria of the heart are in need of cardioversion and when the time between the immediately successive ventricular activations is greater than the preselected minimum time interval and less than a preselected maximum time interval.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
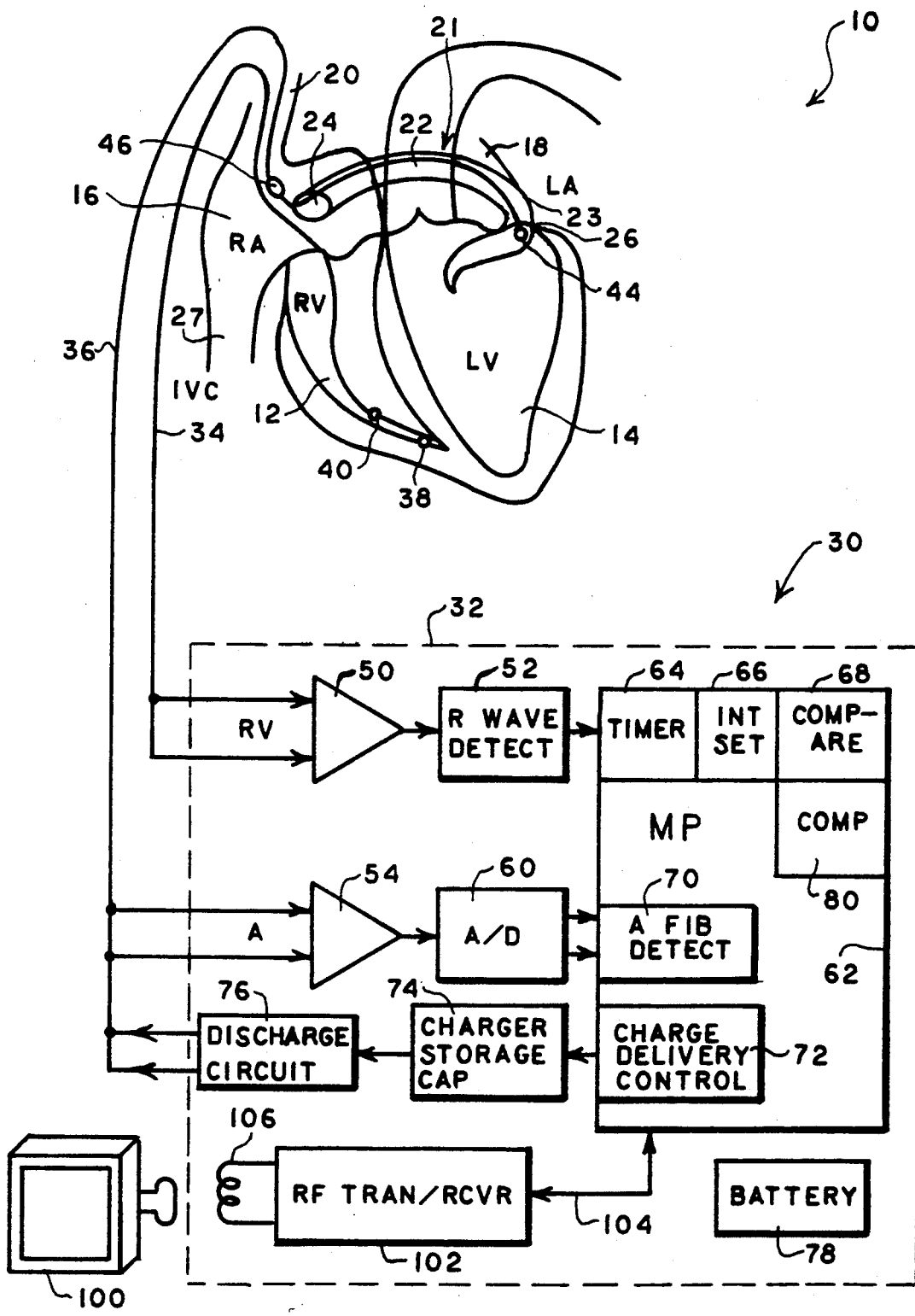
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "ventricular activations" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12 as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, an R wave detector 52, and a second sense amplifier 54. The first sense amplifier 50 and the R wave detector 52 form a first detecting means which together with the first lead 34 to which sense amplifier 50 is coupled, senses ventricular activations of the right ventricle 12. The second sense amplifier 54 forms a second detecting means which, together with the first electrode 44 and second electrode 46 of the second lead 36 to which it is couple detects atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog to digital converter 60 which converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as disclosed in the aforementioned copending U.S. application Ser. Nos. 07/685,130 and 07/856,514 and further as described hereinafter with respect to the flow diagram of FIG. 2. The implementation of the microprocessor 62 in accordance with this embodiment of the present invention results in a plurality of functional stages. The stages include a timer 64, an interval set stage 66, a comparator stage 68, an atrial arrhythmia detector in the form of an atrial fibrillation detector 70, a charge delivery and energy control stage 72 and a computation stage 80.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and coveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, the microprocessor 62 receives programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in interval memory or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 74 of the type well known in the art which charges a storage capacitor to a predetermined voltage level and a discharge circuit 76 for discharging the storage capacitor within circuit 74 by a predetermined amount to provide a controlled discharge output of electrical energy when required to the atria of the heart. To that end, the discharge circuit 76 is coupled to the first electrode 44 and the second electrode 46 of the second lead 36 for applying the cardioverting or defibrillating electrical energy to the atria. Lastly, the defibrillator 30 includes a depletable power source 78, such a lithium battery, for providing power to the electrical components of the atrial defibrillator 30.

The sense amplifier 50 and the R wave detector 52 continuously detect the occurrence of ventricular activations of the right ventricle 12. As disclosed in the aforementioned copending U.S. application Ser. Nos. 07/685,130 and 07/856,514, herein incorporated by reference, when the time intervals between immediately successive R waves indicate the probability of an episode of atrial fibrillation, the microprocessor 62 enables the atrial fibrillation detector 70, sense amplifier 54, and the analog to digital converter 60. If the atrial fibrillation detector 70 determines that the atria 16 and 18 are in fibrillation and thus in need of cardioversion, the charged delivery control 72 causes the charger and storage capacitor circuit 74 to charge the storage capacitor within circuit 74. The operation of the atrial defibrillator 30 then enters the implementation illustrated in the flow diagram of FIG. 2.

Figure 2:
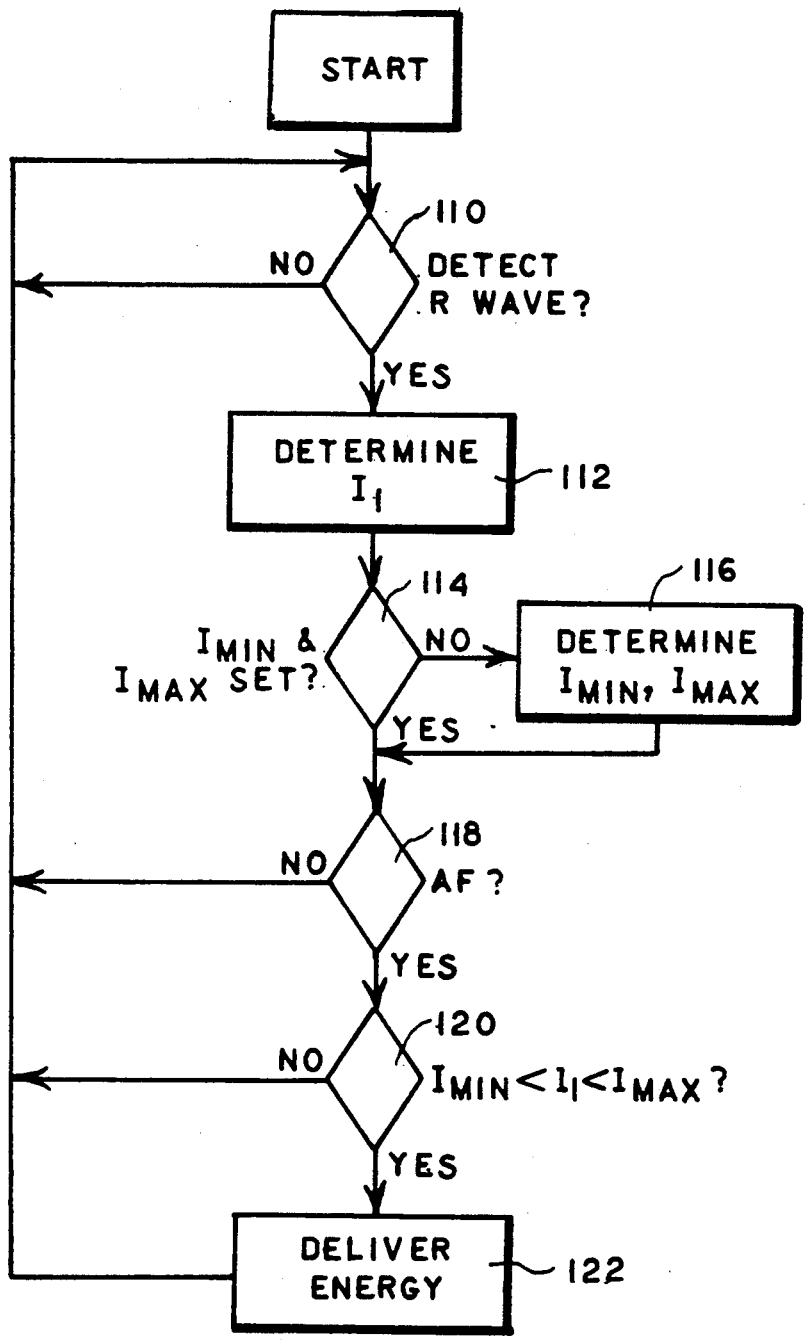
FIG. 2 is a flow diagram illustrating the manner in which the atrial defibrillator of FIG. 1 may be implemented in accordance with the present invention for applying defibrillating or cardioverting electrical energy to the atria of the heart with reduced risk of inducing ventricular fibrillation.

Referring now to FIG. 2, the microprocessor 62 first, in step 110, determines whether a ventricular activation (R wave) has been detected by sense amplifier 50 and the R wave detector 52. If an R wave has not been detected, the microprocessor returns. If an R wave has been detected, the microprocessor then in step 112 determines the time between the last two immediately successive detected R waves. In doing so, the microprocessor interrogates the timer 64 which times, responsive to the sense amplifier 50 and R wave detector 52, the time between immediately successive ventricular activations of the heart 10. Once the last R wave to R wave time interval is determined in step 112, the microprocessor proceeds to step 114 to determine whether minimum and maximum time intervals have been set. In performing step 114, the microprocessor interrogates the interval set stage 66 to determine if the minimum and maximum time intervals have been set. The minimum and maximum time intervals may be set from external to the implanted atrial defibrillator 30 by means of the external controller 100 and the transmitter/receiver 102. If the minimum and maximum time intervals have not been set from external to the atrial defibrillator 30, the atrial defibrillator then determines the minimum and maximum time intervals in step 116. In performing step 116, the computation stage 80 computes the average cardiac cycle interval responsive to and based upon the last predetermined number, such as eight, consecutive R waves detected by sense amplifier 50 and R wave detector 52 and timed by timer 64. Once the average cardiac interval is determined, the microprocessor sets the minimum time interval equal to the average cardiac interval and the computation stage 80 computes the maximum time interval based upon a multiple of the computed average cardiac cycle interval. In accordance with this preferred embodiment, the maximum time interval is preferably the computed average cardiac cycle interval multiplied by 2.0. In accordance with this preferred embodiment, the minimum time interval may be in the range of 300 to 500 milliseconds and the maximum time interval may be in the range of 600 milliseconds to 1 second.

Once the minimum and maximum time intervals are determined in step 116 or if the minimum and maximum time intervals are otherwise preselected as previously described, the atrial defibrillator then proceeds to step 118 to determine whether atrial fibrillation is still occurring. In performing step 118, the microprocessor interrogates the atrial fibrillation detector 70. If the atrial fibrillation detector 70 indicates that the atrial fibrillation has ceased, the microprocessor 62 returns. However, if the atrial fibrillation has persisted, the microprocessor then advances to step 120 wherein it determines if the time between the last two immediately successive ventricular activations as determined in step 112 is greater than the minimum time interval and less than the maximum time interval. If it is not, the microprocessor returns and will not apply the cardioverting or defibrillating electrical energy to the atria of the heart because the present cardiac rate is too high or because the present cardiac rate is suspected to be highly variable. In either case, and R on T condition may be present indicating that the cardioverting or defibrillating electrical energy should not be applied to the heart at this time.

If in step 120 the microprocessor 62 determines that the time between the last two immediately successive ventricular activations is greater than the preselected minimum time interval ($I_{min}$) and less than the preselected maximum time interval ($I_{max}$), the charge delivery control stage 72 of microprocessor 62 causes the discharge circuit 76 to immediately discharge the electrical energy stored in the storage capacitor of circuit 74 for applying the cardioverting or defibrillating electrical energy to the atria 16 and 18 of the heart 10 in accordance with step 122. Since the microprocessor 62 is able to process steps 110 through 120 very quickly after the occurrence of the last detected ventricular activation, the discharge circuit 76 will apply the cardioverting electrical energy to the atria of the heart substantially coincident or in synchronism with the last detected ventricular activation.

Hence, as can be seen from the foregoing, the timer 64 times the time between immediately successive ventricular activations which include a first ventricular activation and an immediately following second ventricular activation. If the atria are in need of cardioversion, and if the time between the immediately successive ventricular activations is greater than the preselected minimum time interval and less than the preselected maximum time interval, the discharge circuit 76 will apply the cardioverting electrical energy to the atria of the heart substantially coincident with the second ventricular activation.

As a result of the foregoing, the atrial defibrillator of the present invention precludes the application of cardioverting or defibrillating electrical energy to the atria of the heart in the presence of a possible vulnerable condition resulting from a cardiac rate which is too high or a cardiac rate which is suspected of being highly variable. In either case, the atrial defibrillator of the present invention greatly reduces the risk of inducing ventricular fibrillation during the application of cardioverting or defibrillating electrical energy to the atria of the heart.

While a particular embodiment of the present invention has been shown and described, modifications may be made. For example, the interval timing of the present invention may be utilized to advantage in an external atrial defibrillator wherein an electrode or electrodes adhered to the surface of the skin of a patient are employed along with an R wave detector for detecting ventricular activations and surface pad electrodes are utilized for applying the cardioverting electrical energy to the atria of the heart. Such surface detecting and pad electrodes are well known in the art. Hence, it is therefore intended in the appended claims to cover all such changes and modifications which fall within the true spirit and scope of the invention.

What is claimed is:

1. An implantable atrial defibrillator for providing cardioverting electrical energy to the atria of a human heart in need of cardioversion, said atrial defibrillator comprising:

first detecting means for detecting ventricular activations of the heart;

second detecting means for detecting atrial activity of the heart;

atrial fibrillation detecting means responsive to said second detecting means for determining when the atria of the heart are in need of cardioversion; and cardioverting means for applying said cardioverting electrical energy to the atria of the heart when the atria of the heart are in need of cardioversion and when the time between immediately successive ventricular activations is greater than a preselected minimum time interval.

2. An atrial defibrillator as defined in claim 1 further including means for determining said minimum time interval responsive to the ventricular activations of the heart detected by said first detecting means.

3. An atrial defibrillator as defined in claim 1 further including timing means responsive to said first detecting means for timing the time between said immediately successive ventricular activations of the heart.

4. An atria defibrillator as defined in claim 1 wherein said immediately successive ventricular activations include a first ventricular activation and an immediately following second ventricular activation and wherein said cardioverting means applies said cardioverting electrical energy to the atria of the heart substantially coincident with said second ventricular activation.

5. An atrial defibrillator as defined in claim 1 wherein said cardioverting means applies said cardioverting electrical energy to the atria of the heart when the atria of the heart are in need of cardioversion and when said time between said immediately successive ventricular activations is greater than said preselected minimum time interval and less than a preselected maximum time interval.

6. An atrial defibrillator as defined in claim 5 further including means for determining said minimum and maximum time intervals responsive to the ventricular activations of the heart detected by said first detecting means.

7. An atrial defibrillator as defined in claim 5 further including timing means responsive to said first detecting means for timing the time between said immediately successive ventricular activations of the heart.

8. An atrial defibrillator as defined in claim 5 wherein said immediately successive ventricular activations include a first ventricular activation and an immediately following second ventricular activation and wherein said cardioverting means applies said cardioverting electrical energy to the atria of the heart substantially coincident with said second ventricular activation.

9. A method of applying cardioverting electrical energy to the atria of a human heart in need of cardioversion, said method including the steps of:
   detecting ventricular activations of the heart;
   detecting atrial activity of the heart;
   determining, responsive to said detected atrial activity of the heart, when the atria of the heart are in need of cardioversion; and
   applying said cardioverting electrical energy to the atria of the heart when the atria of the heart are in need of cardioversion and when the time between immediately successive ventricular activations is greater than a preselected minimum time interval.

10. A method as defined in claim 9 wherein said immediately successive ventricular activations include a first ventricular activation and an immediately following second ventricular activation, and wherein said applying step includes applying said cardioverting electrical energy to the atria of the heart substantially coincident with said second ventricular activation.

11. A method as defined in claim 9 wherein said applying step further includes applying said cardioverting electrical energy to the atria of the heart when the atria of the heart are in need of cardioversion and when said time between said immediately successive ventricular activations is greater than said preselected minimum time interval and less than a preselected maximum time interval.

12. A method as defined in claim 11 wherein said immediately successive ventricular activations include a first ventricular activation and an immediately following second ventricular activation, and wherein said applying step includes applying said cardioverting electrical energy to the atria of the heart substantially coincident with said second ventricular activation.

13. An atrial defibrillator for providing cardioverting electrical energy to the atria of a human heart, said atrial defibrillator comprising:
   detecting means for detecting ventricular activations of the heart; and
   cardioverting means for applying said cardioverting electrical energy to the atria of the heart when the time between immediately successive ventricular activations detected by said detecting means is greater than a preselected minimum time interval.

* * * * *